United States Patent [19]

Austin

[11] Patent Number: 5,112,871
[45] Date of Patent: May 12, 1992

[54] ANTI-MICROBIAL BROMO-NITRO COMPOUNDS

[75] Inventor: Peter W. Austin, Bury, England

[73] Assignee: Imperial Chemical Industries PLC, Millbank, England

[21] Appl. No.: 429,629

[22] Filed: Oct. 31, 1989

[30] Foreign Application Priority Data

Nov. 30, 1988 [GB] United Kingdom ................ 8827899

[51] Int. Cl.$^5$ .................... A01N 33/20; C07C 205/01
[52] U.S. Cl. .................................. 514/727; 514/740; 568/713
[58] Field of Search ............... 514/476, 478, 740, 727; 568/713

[56] References Cited

FOREIGN PATENT DOCUMENTS 1057131  5/1967  United Kingdom .

*Primary Examiner*—Marianane Cintins
*Assistant Examiner*—Margaret J. Argo
*Attorney, Agent, or Firm*—William E. Dickheiser

[57] ABSTRACT

A bromo-nitro compound of the general formula

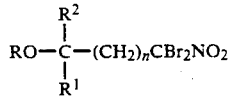

where R, $R^1$ and $R^2$ can be hydrogen, or a hydrocarbyl group and R can also be $R^3CO$ or $R^3NHCO$ and n has a value of at least one. R and $R^1$ can both be hydrogen. The value of n is typically one. Compounds of this type have anti-microbial properties, expecially anti-bacterial properties. The compounds can be used as industrial biocides, especially in water treatment.

6 Claims, No Drawings

ANTI-MICROBIAL BROMO-NITRO COMPOUNDS

The present invention relates to a class of compounds which have anti-microbial properties, compositions containing such compounds, a process for the production of such compounds and the use of the compound.

Compounds which have anti-microbial properties are potentially useful as industrial biocides. Spoilage, particularly that caused by bacteria and fungi, can be prevented or reduced by the use of industrial biocides. Thus, such materials can be used in applications such as the preservation of paints, lattices, adhesives, personal care products, leather, wood, metal working fluids and cooling water.

2-Bromo-1,3-dihydroxy-2-nitropropane is a commercially available material which can be used for the treatment of water, particularly cooling water. In J. Med. Chem. 17 (1974), pages 977 to 981, the compound 2-acetoxy-1,1-dibromo-1-nitropropane, and the compound 2-acetoxy-1,1-dibromo-1-nitrobutane, are described and are disclosed as having anti-bacterial properties. British Patent 1,057,131 discloses compounds of the general formula $$R_1R_3C(OH)CR_2BrNO_2$$

where $R_1$ is hydrogen or alkyl, $R_3$ is hydrogen or forms a ring with $R_1$ and $R_2$ is hydrogen, methyl, ethyl, hydroxymethyl or bromine. Compound of this type are indicated to have antibacterial and antifungal properties. A range of compounds is disclosed but several of these are explicitly stated to have a tendency to be unstable in the presence of water. Only two compounds are stated to be substantially stable in the presence of water and in both of these the group $R_2$ is a hydroxymethyl group as in 2-bromo-2-nitropropane-1,3-diol which is stated to be the especially preferred compound. Japanese Patent Application (Kokai) No. 61(1986)024502 also discloses bromonitropropane derivatives as 1,1-dibromo-1-nitro-2-acetoxypropane as being useful as fungicides and as preservatives for coolants in various industries. The compounds of Kokai 61(1986)024502 are indicated to be more effective than 2-bromo-1,3-dihydroxy-2-nitropropane.

We have now found other bromo-nitro compounds which have improved anti-microbial, particularly improved anti-bacterial properties.

According to the present invention there is provided a bromo-nitro compound of the general formula

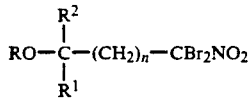

where:
R is hydrogen, a hydrocarbyl group, a substituted hydrocarbyl group, a group $R^3CO$ or a group $R^3NHCO$;
$R^1$ and $R^2$ are, independently, hydrogen, a hydrocarbyl group or a substituted hydrocarbyl group;
$R^3$ is a hydrocarbyl group or a substituted hydrocarbyl group; and
n has a value of at least one.

If the group R is other than hydrogen, it may be a straight or branched chain alkyl, alkenyl or alkynyl group, which may be substituted, or R can be a group $R^3CO$ or $R^3NHCO$. If any of the groups R, $R^1$, $R^2$ and $R^3$ are substituted hydrocarbyl groups, the substituent may be, for example, aryl groups, hydrocarbyloxy groups, ester (that is acyloxy) groups, halogen atoms, or nitrile groups. The group R is conveniently the group $R^3CO$ and most conveniently is hydrogen. If the group R is a hydrocarbyl group, a substituted hydrocarbyl group, a group $R^3CO$ or a group $R^3NHCO$, it typically contains not more than ten carbon atoms and especially not more than six carbon atoms.

If either or both of the groups $R^1$ and $R^2$ are other than hydrogen, they are typically alkyl, alkenyl or alkynyl groups, particularly alkyl groups and in general contain not more than six carbon atoms and especially not more than four carbon atoms. The groups $R^1$ and $R^2$ may be the same or different. Useful compounds inn accordance with the invention are those wherein at least one of the groups $R^1$ and $R^2$ is hydrogen, especially wherein both $R^1$ and $R^2$ are hydrogen.

Thus, as a particular embodiment of the present invention there is provided a bromo-nitro compound of the general formula:

$$RO-CH_2(CH_2)_nCBr_2NO_2$$

where R and n are both as hereinbefore defined.

If the group R is $R^3CO$ or $R^3NHCO$, the group $R^3$ is typically an alkyl group containing not more than four carbon atoms and especially is a methyl or ethyl group.

n is typically an integer and generally does not exceed eight and especially is not more than four. If the value of n is not integral, the compound is a mixture of compounds in which the value of n is different. A useful compound in accordance with the present invention is one in which the value of n is one.

Bromo-nitro compounds in accordance with the present invention which have useful properties are 1,1-dibromo-1-nitropropan-3-ol and the esters thereof, for example the acetate and propionate.

The compounds of the present invention are conveniently prepared by brominating a precursor compound which does not contain bromine. Conveniently, a nitroalkanol is brominated and the compound produced may be further reacted, for example may be reacted with an appropriate acid, acid halide or acid anhydride.

More specifically, a compound of the formula:

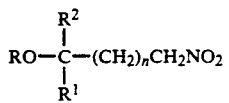

is brominated.

The compound obtained is a compound in accordance with the present invention and, if R is hydrogen, the compound can be further reacted, conveniently with an acid, acid halide or acid anhydride to form a compound in which R is a group $R^3CO$. Alternatively, a compound in which R is a group $R^3NHCO$ can be prepared by reacting the alcohol (R is hydrogen) with an isocyanate of the formula $R^3NCO$.

Bromination can be effected using any suitable bromination technique, for example by contacting with bromine. Reaction with bromine is preferably effected in the presence of an alkaline medium. The reaction conditions are dependent on the particular compound being brominated but it is generally unnecessary to use temperatures above 50° C. The reaction is conveniently effected at a temperature not greater than ambient temperature, for example a temperature in the range 0° to 5° C.

The nitro compound may be prepared by known procedures, for example 3-nitropropan-1-ol may be prepared using the procedure described in Rec. Trav. Chim. Pays Bas 16 (1897) 193.

Compounds which are esters can be prepared from the corresponding alcohol and the ester formed may be recovered from the reaction mixture by dilution with ice-cold water, extracting with ether, washing and drying the ether extract and thereafter evaporating off the ether solvent.

The product obtained by the bromination step, or by bromination followed by esterification, may be purified by any suitable technique. A convenient method of purification is using a chromatographic technique, for example by flash chromatography, or by fractional distillation.

The bromo-nitro compounds of the present invention have anti-microbial properties and, in particular, show considerable activity against bacteria.

Thus, as a further aspect of the present invention, there is provided a biocide composition which contains at least one compound of the formula

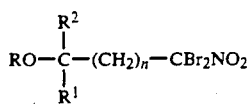

where R, $R^1$, $R^2$ and n are all as hereinbefore defined.

The compositions show particularly useful anti-bacterial activity and hence are potentially useful in environments in which bacteria can cause spoilage. Thus, the compositions may be used to provide wet state preservation, for example as a cutting fluid preservative or in industrial water systems such as in cooling water. The compositions may be used to provide in the can preservation of materials such as paints. The compositions may be used in personal care formulations including shampoo.

The bromo-nitro compounds of the present invention are soluble in many polar solvents, including water, although the solubility is dependent on the nature of R, $R^1$ and $R^2$, and on the value of n, for example on the chain length and degree of branching of the groups R, $R^1$ and $R^2$.

The biocide composition of the present invention may consist only of the bromo-nitro compound or of a mixture of bromo-nitro compounds in which R, $R^1$, $R^2$ or, particularly, n differ. However, the biocide composition typically contains other components, for example an effective amount of the bromo-nitro compound together with a carrier material. The carrier material may be any inert solid such as silica, alumina or talc, onto the surface of which the bromo-nitro compound is absorbed. However, in general, the carrier is a liquid medium having little, if any, anti-microbial activity. The biocide composition may comprise a solution, suspension or emulsion of the bromo-nitro compound in a suitable liquid medium such as water. Alternatively, a mixture of liquids may be used, one being a solvent for the bromo-nitro compound and the other being a non-solvent, and using such a mixture the composition typically comprises an emulsion of droplets of a solution of the bromo-nitro compound in the solvent therefor dispersed in the non-solvent. If a suspension or emulsion is used, this conveniently contains a surface active agent which is effective to maintain the non-continuous phase as a suspension or emulsion. Any surface active agent known for use in biocide compositions may be used in such a system, for example alkylene oxide adducts of fatty alcohols, alkyl phenols and amines such as ethylene diamine.

The amount of the bromo-nitro compound which is present in the biocide composition may be just sufficient to have an antimicrobial effect or the bromo-nitro compound may be present in a substantially greater proportion. It will be appreciated that the biocide composition may be provided as a concentrated solution which is subsequently diluted for use as an antimicrobial material. Thus, the amount of the bromo-nitro compound which is present in the biocide composition is typically in the range from 0.0001% up to 30%, and especially up to 10%, by weight of the biocide composition.

The biocide composition has anti-microbial activity and is especially effective in providing anti-bacterial activity. Thus, the compositions can be used for the treatment of various media to inhibit the growth of micro-organisms.

As a further aspect of the present invention there is provided a method for inhibiting the growth of micro-organisms on, or in, a medium which comprises treating the medium with at least one bromo-nitro compound as hereinbefore defined.

The bromo-nitro compounds can be used in conditions in which micro-organisms, especially bacteria, grow and cause problems. Systems in which micro-organisms cause problems include liquid, particularly aqueous, systems such as cooling water liquors, metal working fluids, geological drilling lubricants, polymer emulsions and surface coating compositions such as paints, varnishes and lacquers, personal care formulations such as shampoos and also solid materials such as wood and leather. The bromo-nitro compounds can be included in such materials and are particularly useful when incorporated into an industrial water system or a metal working fluid to which they provide anti-bacterial characteristics. The term "industrial water system" includes cooling water systems, paper mill water, secondary-oil recovery injection water and other water systems used industrially and liable to spoilage by bacteria or other micro-organisms.

As a particular aspect of the present invention there is provided an industrial water system, particularly a cooling water liquor which contains an effective amount of a bromo-nitro compound in accordance with the present invention.

The industrial water system is particularly a cooling water liquor and may be any cooling water which is susceptible to the growth of micro-organisms for example cooling tower water. The amount of the bromo-nitro compound which is present in the cooling water liquor is typically in the range from 0.0001% up to 2% by weight. In general the minimum amount of the bromo-nitro compound is 0.001% by weight. The amount of the bromo-nitro compound typically does not exceed 1% by weight relative to the total weight of the cooling water liquor. The amount of the bromo-nitro compound in the cooling water liquor is especially in the range of from 0.001% up to 0.1% by weight.

The bromo-nitro compounds provide anti-bacterial properties to the cooling water liquor and are effective in controlling the amount of the slime produced. The bromo-nitro compounds are particularly useful since they appear to have enhanced water stability compared to many of the compounds disclosed in British Patent 1,057,131, even compounds which are isomeric with those of the present invention.

The bromo-nitro compounds of the present invention may be the only antimicrobial compound or may be used together with other compounds having antimicrobial characteristics. Thus, a mixture of different bromo-nitro compounds in accordance with the present invention may be used. Alternatively, at least one bromo-nitro compound in accordance with the present invention may be used together with one or more known antimicrobial compounds. The use of a mixture of antimicrobical compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the bromo-nitro compounds of the present invention with other antimicrobial compounds typically contains from 1 to 99% by weight, relative to the weight of total antimicrobially active compounds, of the bromo-nitro compounds, particularly from 40 to 60% by weight of the bromo-nitro compounds.

As examples of known antimicrobial compounds which may be used, together with the bromo-nitro compounds of the present invention, there may be mentioned quaternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethy-tetradecylammonium chloride; benzyldimethyl($C_{12}$–$C_{18}$ alkyl)ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecylbenzyltrimethylammonium chloride; benzyldimethyl($C_{12}$–$C_{18}$ alkyl)ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; tetrakis(hydroxymethyl)acetylene diurea; 1-(hydroxymethyl)-5,5-dimethylhydantoin and imidazolidinyl urea; amino compounds such as 1,3-bis(2-ethylhexyl)-5-methyl-5-aminohexahydropyrimidine; hexamethylene tetraamine; 1,3-bis(4-aminophenoxy)propane; and 2-[(hydroxymethyl)amino]ethanol; imidazole derivatives such as 1[2-(2,4-dichlorophenyl)-2-(2-propenyloxy)ethyl]-1H-imidazole; 2-(methoxycarbonylamino)-benzimidazole; nitrile compounds such as 2,4,5,6-tetrachloroisophthalodinitrile and 1,2-dibromo-2,4-dicyanobutane; thiocyanate derivatives such as methylene bis thiocyanate; zinc compounds or complexes such as zinc-2-pyridinethiol-N-oxide; tin compounds or complexes such as tributyltin-oxide, chloride, naphthoate, benzoate or 2-hydroxybenzoate; thiazole derivatives such as 2-(thiocyanomethylthio)-benzthiazole; and mercaptobenzthiazole; isothiazole derivatives such as 5-chloro-2-methyl-4-isothiazolin-3-one and the magnesium salts thereof; 2-methyl-4-isothiazolin-3-one; 1,2-benzisothiazolin-3-one and the alkali metal, ammonium and amine salts thereof; and 2-n-octyl-4-isothiazolin-3-one; nitro compounds such as tris(hydroxymethyl)nitromethane; 5-bromo-5-nitro-1,3-dioxane and 2-bromo-2-nitropropane-1,3-diol; aldehydes and derivatives such as gluteraldehyde (pentanedial)p-chlorophenyl-3-iodopropargyl formaldehyde and glyoxal; amides such as chloroacetamide; N,N-bis(hydroxymethyl)chloracetamide; N-hydroxymethyl-chloracetamide and dithio-2,2-bis(benzymethyl amide); guanidine derivatives such as poly hexamethylene biguanide and 1,6-hexamethylene-bis[5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichlorophenoxy)phenol; thio-bis(4-chlorophenol) and 2-phenylphenol; sulphone derivatives such as chloromethyl-diiodomethyl sulphone and hexachlorodimethyl sulphone.

The bromo-nitro compounds of the present invention are particularly useful when incorporated into an industrial water system and hence, if used with other compounds having antimicrobial characteristics, these other compounds are advantageously compounds of the type used in industrial water systems. Compounds which may be used in industrial water systems include, inter alia, 5-chloro-2-methyl-4-isothiazolin-3-one; 2-methyl-4-isothiazolin-3-one and mixtures thereof; quaternary ammonium compounds; methylene bis thiocyanate; 3,5-dimethyltetrahydro-1,3,5-2H-thiadiazine-2-thione; 2,2-dibromo-3-nitrilopropionamide; 2-bromo-2-nitropropanediol; hexachlorodimethylsulphone; bis(1,4-bromoacetoxy)-2-butene; 2,3-dibromopropionaldehyde; beta-bromo-beta-nitrostyrene; 2-bromo-4-hydroxyacetophenone; glutaraldehyde and derivatives of fatty amines such as coco-alkylamine acetate, dodecylguanidine acetate and coco-amine acetate.

Further aspects of the present invention are described in the following illustrative examples. In the following tests and examples, all parts are by weight unless stated to the contrary.

In the following examples, the products obtained were subjected to microbiostatic evaluation and some products were also subjected to evaluation for bactericidal activity in an aqueous medium. The microbiological testing was effected, under sterile conditions throughout, as follows:

In the microbiological testing, the products were tested for anti-microbial activity against bacteria and/or fungi. In some of the testing, bacteria used were one or more of *Escherichia coli, Staphylococcus aureus,* and *Pseudomonas aeruginosa*, whilst the fungi used were one or more of *Aspergillus niger, Aureobasidum pullulans, Cladosporium sphaerospermum, Aspergillus versicolor* and *Chaetomium globosum*. These test organisms will be referred to hereafter as EC, SA, PA, AN, AP, CS, AV and CG respectively. Other tests were carried out in which the bacteria *Pseudomonas fluorescens* and Flavobacterium were used.

Microbiostatic Evaluation

The material to be tested was dissolved in a suitable solvent and the solution obtained diluted with a further quantity of the same solvent to give a desired product concentration.

To a suitable agar medium was added a quantity of the product solution to give a desired concentration of the product. The agar medium containing the product was poured into petri dish plates and allowed to set.

The test organisms were surface inoculated onto the test plates by means of a multi-point inoculator. Each test plate was inoculated with both bacteria and fungi. The plates were incubated for four days at 25° C.

At the end of the incubation period, the plates were assessed visually for growth of the micro-organisms. The concentration of the product which inhibited the growth of a particular micro-organism was recorded.

EXAMPLE 1

10.5 parts of 3-nitropropan-1-ol (prepared from 1-hydroxy-3-iodopropane and silver nitrite as described in Rec. Trev. Chim. Pays Bas 16 (1897), 193) were stirred at 0°-5° C. with 10 parts of water. A solution of 10 parts of sodium hydroxide in 60 parts of ice-cold (0°-5° C.) water were then added dropwise over a period of 30 minutes. The mixture obtained was stirred at 0°-5° C. for a further one hour and 33 parts of bromine at 0°-5° C. were added dropwise to the stirred mixture over a period of half an hour whilst maintaining the temperature at 0°-5° C. The mixture was stirred at 0°-5° C. for a further half an hour and 100 parts of chloroform were then added. The chloroform was allowed to settle out and was separated.

The chloroform solution was washed with 50 parts of a 0.5% w/v aqueous solution of sodium bisulphite, then with 50 parts of water and finally dried using anhydrous magnesium sulphate. The mixture was then evaporated to dryness under a water pump vacuum and a bath temperature of less than 40° C. A syrup was obtained which was distilled under reduced pressure and the fraction distilling at 125° C. (bath temperature) and 0.6 mm pressure, was collected.

14.2 parts of 1,1-dibromo-1-nitropropan-3-ol were obtained as a colourless oil which slowly solidified, melting point 22°-25° C.

By analysis the composition was found to be C 13.7% wt; H 2.0% wt; N 5.3% wt and Br 60.9% wt. $C_3H_5Br_2NO_3$ requires $C_{13.7}\%$ wt; H 1.9% wt; N 5.3% wt and Br 60.8% wt.

Carbon -13 NMR showed three peaks at 84.33, 60.08 and 50.24 ppm, this being entirely consistent with the compound 1,1-dibromo-1-nitropropan-3-ol.

EXAMPLE 2

The compound of Example 1 was evaluated against a range of bacteria and fungi using the microbiostatic evaluation procedure described previously herein. By way of comparison a commercially available biocide containing 2-bromo-1,3-dihydroxy-2-nitropropane as the active ingredient was also evaluated under the same conditions. A further comparison was effected using 1,1-dibromo-1-nitropropan-2-ol, which is compound J in British Patent Specification No. 1,057,131 and which is isomeric with the compound of Example 1. The results obtained are set out in the following Table One.

TABLE ONE

| MIC | Compound | | |
|-----|---|---|---|
| (a) | 1 | A | B |
| EC | 10 | 10 | 10 |
| SA | 10 | 10 | 10 |
| PA | 10 | 50 | 10 |
| AN | 5 | 500 | 5 |
| AP | 5 | 500 | 25 |
| CS | 5 | 500 | 5 |
| AV | 5 | 25 | 5 |
| CG | 5 | 500 | 5 |

Notes to Table One
(a) MIC is the minimum inhibitory concentration in ppm of each compound for each of the bacteria or fungi tested.
(b) 1 is the product of Example 1.
A is a commercially available biocide containing 2-bromo-1,3-dihydroxy-2-nitropropane as the active ingredient.
B is 1,1-dibromo-1-nitropropan-2-ol which is isomeric with the product of Example 1.

EXAMPLE 3

Compound 1 and comparative compound B were tested for stability on storage.

0.5% w/v solutions of the compound 1 and of comparative example B were prepared in a 90:10 water/methanol mixture. The solutions were stored at ambient temperature. After being stored for two weeks, both solutions were subjected to HPLC analysis.

The analysis of the solution of compound 1 showed one peak corresponding to 1,1-dibromo-1-nitropropan-3-ol, indicating that no detectable degradation had occurred. The analysis of the solution of comparative compound B showed only 18% of the original 1,1-dibromo-1-nitropropan-2-ol to be present, there being present many other peaks of unknown identity.

EXAMPLE 4

100 cm$^3$ samples of a liquid medium of tap water supplemented with glucose (100 ppm) and ammonium nitrate (2 ppm) and also containing a mixed population of bacteria (predominantly *Pseudomonas fluorescens* and Flavobacterium) were removed from a 5 dm$^3$ reservoir of an open recycling system. The initial bacterial count in the liquid medium was in the range 7.2 to 7.7×10$^7$. The samples were placed in 250 cm$^3$ conical flasks and compounds for testing were added to give concentrations of active ingredient of 200, 100, 25, 6.25 or 1.56 ppm.

The solutions containing the compounds for testing, together with a solution containing no additive, were incubated at 30° C. on an orbital shaker. After incubation periods of 4 and 24 hours, the surviving bacteria were determined by the decimal dilution method using nutrient agar.

The results obtained are set out in Table Two.

TABLE TWO

| Compound | Conc. (ppm) | Survivors (cells/cm$^3$) | |
|---|---|---|---|
| (b) (c) | (d) | 4 hr | 24 hr |
| 1 | 100 | <10 | <10 |
| 1 | 25 | <10 | <10 |
| 1 | 6.25 | 1.2 × 10$^2$ | <10 |
| 1 | 1.56 | >3.0 × 10$^5$ | 1.1 × 10$^3$ |
| B | 100 | <10 | <10 |
| B | 25 | >3.0 × 10$^5$ | <10 |
| B | 6.25 | >3.0 × 10$^5$ | >3.0 × 10$^5$ |
| B | 1.56 | >3.0 × 10$^5$ | >3.0 × 10$^5$ |
| A | 200 | >3.0 × 10$^5$ | 1.3 × 10$^3$ |
| A | 100 | >3.0 × 10$^5$ | >3.0 × 10$^5$ |
| C | 200 | >3.0 × 10$^5$ | <10 |
| C | 100 | >3.0 × 10$^5$ | 1.5 × 10$^4$ |

TABLE TWO-continued

| Compound (b) (c) | Conc. (ppm) (d) | Survivors (cells/cm³) 4 hr | 24 hr |
|---|---|---|---|
| — | NIL | $7.7 \times 10^7$ | $7.3 \times 10^7$ |

Notes to Table Two
(b) is as defined in Notes to Table One.
(c) C is a commercially available biocide containing 2-bromo-2-nitro-1,3-dioxan as the active ingredient.
(d) The concentration is that of the active ingredient.

EXAMPLE 5

Compound 1 and comparative compound B were stored for two weeks as described in Example 3 and the test procedure of Example 4 was repeated using the compounds which had been stored. The activity of comparative compound B was found to be 12.5% of the activity of compound 1 after both compound had been stored.

EXAMPLE 6

2.3 parts of the product of Example 1 and 15 parts of acetic anhydride were stirred at ambient temperature (about 20° C.) and 2 drops of boron trifluoride etherate were added. The mixture was stirred at 20°-25° C. for 16 hours and then added to 200 parts of ice-cold (0°-5° C.) water. The mixture formed was stirred for a further two hours and the mixture was extracted with 200 parts of diethylether. The ether extract was then washed three times using ice-cold (0°-5° C.) saturrated sodium bicarbonate solution, dried using anhydrous magnesium sulphate and then evaporated to dryness.

The product obtained was purified by flash chromatography on silica gel, the fractions eluted with 30-50% of chloroform in petroleum ether being collected.

The acetyl derivative (3-acetoxy-1,1-dibromo-1-nitropropane) was obtained as a colourless oil. The product had a proton NMR showing peaks at 1.95 (singlet), 3.25 (triplet) and 4.3 (triplet) ppm, this being entirely consistent with the acetyl derivative. The infra-red spectrum showed a strong absorption band at 1740 cm$^{-1}$, corresponding to a carbonyl group but there was no hydroxyl absorption at 3300-3600 cm$^{-1}$.

EXAMPLE 7

The procedure of Example 6 was repeated with the exception that acetic anhydride was replaced by a stoichiometric equivalent amount of propionic anhydride.

The propionyl derivative (1,1-dibromo-1-nitro-3-propionoxypropane) was obtained as a colourless oil. The product had a proton NMR showing peaks at 1.1 (triplet), 2.3 (quadruple), 3.3 (triplet) and 4.35 (triplet) ppm, this being entirely consistent with the propionyl derivative. The infra-red spectrum showed a strong absorption band at 1760 cm$^{-1}$, corresponding to a carbonyl group.

EXAMPLES 8 AND 9

The procedure of Example 4 was repeated with the exception that the water contained *Escherichia coli* and the compounds for testing were the products of Examples 6 and 7 in amounts of 2, 10, 50 and 250 ppm. The solutions were incubated for one hour and 24 hours and the surviving bacteria were determined by the decimal dilution method using nutrient agar. The concentration of active ingredient required to reduce the bacteria count from $10^7$ to $<10$ per cm$^n$ were determined and the results are recorded in Table Three.

TABLE THREE

| Example | Compound (e) | Concentration (f) 1 hour | 24 hours |
|---|---|---|---|
| 8 | 6 | 10-50 | <2 |
| 9 | 7 | 10-50 | <2 |

Notes to Table Three
(e) 6 is the product of Example 6
7 is the product of Example 7
(f) The concentration is in ppm of active ingredient and is the concentration required to give a bacterial count of less than 10 per cm after the specified time.

EXAMPLES 10 AND 11

The procedure of Examples 8 and 9 was repeated with the exception that the water contained *Pseudomonas fluorescens*, the concentration of active ingredient was 3.125, 12.5, 50 and 200 ppm and the measurements of bacterial count were made after 4 and 24 hours. The results are given in Table Four.

TABLE FOUR

| Example | Compound (e) | Concentration (f) 4 hour | 24 hours |
|---|---|---|---|
| 10 | 6 | 12.5-50 | 3.125-12.5 |
| 11 | 7 | 12.5-50 | 3.125-12.5 |

Notes to Table Four
(e) and (f) are both as defined in Notes to Table Three.

EXAMPLE 12

A formulation typical of many shampoo formulations was prepared from the following ingredients

| Component (g) | % wt |
|---|---|
| SLES | 16.5 |
| ADAA | 2.0 |
| ADMB | 5.0 |
| NaCl | 1.0 |
| Citric Acid | to pH 7 |
| Water | 75.5 |

Note (g)
SLES is highly concentrated sodium lauryl ethoxy (2EO) sulphate obtainable from Albright and Wilson Limited as Empicol ESB70.
ADAA is an alkyl dialkylolamide obtainable from Albright and Wilson Limited as Empilan 2502.
ADMB is $C_{12}/C_{14}$ alkyl dimethyl betaine obtained from Albright and Wilson Limited as Empigen BB.
NaCl is sodium chloride.

The formulation was prepared by mixing SLES and water, adding ADAA and then ADMB and mixing this well to give a clear homogeneous solution. Aqueous citric acid was added to adjust the pH of the mixture to pH 7 and sodium chloride was finally added.

20 g aliquots of the foregoing mixture were dispensed into glass screw-capped jars. The product of Example 1 was added to the shampoo to give concentrations of 500, 125, 31.25 and 7.8 ppm, by weight, of active ingredient. For comparison, samples of commercially available biocides, which are used in shampoos, were added to other samples of the shampoo formulation, at the same levels. A further sample of the shampoo contained no biocide.

An inoculum which consisted of 0.2 cm³ of a 24 hour culture of *Pseudomonas aeruginosa* (containing $1 \times 10^8$ cells/cm³) was added to each shampoo sample and the samples were incubated in the dark at 25° C.

A 1 cm³ sample of incubated shampoo was removed from each mixture after 24 hours, 48 hours and 7 days and the number of bacterial survivors was determined. The results obtained are set out in Table Five.

TABLE FIVE

| Compound (b) (h) | Conc. (ppm) (d) | Survivors (cells/cm³) | | |
|---|---|---|---|---|
| | | 24 hr | 48 hr | 7 days |
| 1 | 500 | <10 | <10 | <10 |
| 1 | 125 | <10 | <10 | <10 |
| 1 | 31.25 | <10 | <10 | <10 |
| 1 | 7.8 | <10 | <10 | <10 |
| D | 500 | <10 | <10 | <10 |
| D | 125 | <10 | <10 | <10 |
| D | 31.25 | <10 | <10 | <10 |
| D | 7.8 | <10 | <10 | <10 |
| E | 500 | $15 \times 10^5$ | $>3.0 \times 10^6$ | $>3.0 \times 10^6$ |
| E | 100 | $20 \times 10^5$ | $>3.0 \times 10^6$ | $>3.0 \times 10^6$ |
| E | 31.25 | $12 \times 10^5$ | $>3.0 \times 10^6$ | $>3.0 \times 10^6$ |
| E | 7.8 | $25 \times 10^5$ | $>3.0 \times 10^6$ | $>3.0 \times 10^6$ |
| — | NIL | $19 \times 10^5$ | $80 \times 10^6$ | $>3.0 \times 10^6$ |

Notes to Table Five (b) is as defined in Notes to Table One.

(d) is as defined in Notes to Table Two.

(h) D is a commercially available biocide containing a mixture of 5-chloro-2-methyl-4-isothiazolin-3-one and 2-methyl-4-isothiazolin-3-one as the active ingredient.

E is a commercially available biocide containing a mixture of sodium salts of the alkyl esters of 4-hydroxybenzoic acid as the active ingredient.

I claim:

1. A compound of the formula I:

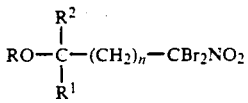

where:

R is hydrogen;

R¹ and R² are independently selected from the group consisting of hydrogen, $C_1$-$C_6$ alkyl, $C_2$-$C_6$ alkenyl and $C_2$-$C_6$ alkynyl; and n has a value of at least one and not more than eight.

2. The compound of claim 1 wherein at least one of R¹ and R² is hydrogen.

3. A biocide composition which contains from 0.0001% up to 30% by weight of the composition of at least one compound of formula I as claimed in claim 1 together with a carrier material.

4. The composition of claim 3 wherein the carrier material is a liquid in which the compound of formula I is soluble.

5. A compound of the formula II:

wherein

R is hydrogen; and n has a value of at least one and not more than four.

6. 1,1-Dibromo-1-nitropropan-3-ol.

* * * * *